(12) United States Patent
Yamagata et al.

(10) Patent No.: US 11,612,345 B2
(45) Date of Patent: Mar. 28, 2023

(54) INPUT DEVICE, MEASUREMENT SYSTEM, AND COMPUTER-READABLE MEDIUM

(71) Applicants: Hideaki Yamagata, Kanagawa (JP); Noriyuki Tomita, Ishikawa (JP)

(72) Inventors: Hideaki Yamagata, Kanagawa (JP); Noriyuki Tomita, Ishikawa (JP)

(73) Assignee: RICOH COMPANY, LTD., Tokyo (JP)

( * ) Notice: Subject to any disclaimer, the term of this patent is extended or adjusted under 35 U.S.C. 154(b) by 605 days.

(21) Appl. No.: 16/293,828

(22) Filed: Mar. 6, 2019

(65) Prior Publication Data
US 2019/0282111 A1   Sep. 19, 2019

(30) Foreign Application Priority Data

Mar. 15, 2018 (JP) .............................. JP2018-048652
Dec. 27, 2018 (JP) .............................. JP2018-246035

(51) Int. Cl.
*A61B 5/00* (2006.01)
*A61B 5/245* (2021.01)
(Continued)

(52) U.S. Cl.
CPC .............. *A61B 5/245* (2021.01); *A61B 5/062* (2013.01); *A61B 5/369* (2021.01); *A61B 5/4064* (2013.01);
(Continued)

(58) Field of Classification Search
CPC ......... A61B 5/245; A61B 5/062; A61B 90/39; A61B 5/7475; A61B 5/369; A61B 5/4064;
(Continued)

(56) References Cited

U.S. PATENT DOCUMENTS 5,967,982 A * 10/1999 Barnett .................. A61B 90/10
378/206
2002/0087101 A1* 7/2002 Barrick ................ A61B 5/1126
600/587
(Continued)

FOREIGN PATENT DOCUMENTS

JP     H07-124133     5/1995
JP     2611188        2/1997
(Continued)

OTHER PUBLICATIONS

Bruns et al., "Application of Amplitude-integrated EEG Monitor (Cerebral Function Monitor) to Neonates", 2017, Journal of Visualized Experiments (Year: 2017).*
(Continued)

*Primary Examiner* — Katherine L Fernandez
*Assistant Examiner* — Brooke Lyn Klein
(74) *Attorney, Agent, or Firm* — Harness, Dickey & Pierce, P.L.C.

(57) ABSTRACT

An input device is to input a shape of a measurement target is response to a signal transmitted from a stylus pen, to determine positional relation between a position of a marker and a shape of the measurement target. The marker is attached to the measurement target and detectable by a cerebral-function measuring device. The input device includes a controller, and a display unit. The controller is configured to generate a screen in which a three dimensional shape of the measurement target and a guide of a position to be acquired next with the stylus pen are superimposed. The display unit is configured to display the screen generated by the controller, on a display portion.

19 Claims, 12 Drawing Sheets

(51) Int. Cl.
  *G01R 33/48* (2006.01)
  *A61B 5/369* (2021.01)
  *G16H 30/20* (2018.01)
  *G06F 3/0354* (2013.01)
  *A61B 90/00* (2016.01)
  *A61B 5/06* (2006.01)

(52) U.S. Cl.
  CPC ............ *A61B 5/7475* (2013.01); *A61B 90/39* (2016.02); *G01R 33/4806* (2013.01); *G06F 3/03545* (2013.01); *G16H 30/20* (2018.01)

(58) Field of Classification Search
  CPC .. G06F 3/03545; G16H 30/20; G01R 33/4806
  See application file for complete search history.

(56) References Cited

U.S. PATENT DOCUMENTS

| | | | | |
|---|---|---|---|---|
| 2004/0105086 | A1* | 6/2004 | Leitner | A61B 17/1714 |
| | | | | 356/3 |
| 2007/0032720 | A1* | 2/2007 | Koivukangas | A61B 5/055 |
| | | | | 600/407 |
| 2011/0191084 | A1* | 8/2011 | Cooke | A61B 6/583 |
| | | | | 703/11 |
| 2013/0109996 | A1* | 5/2013 | Turnbull | A61B 5/7203 |
| | | | | 600/544 |
| 2014/0078517 | A1* | 3/2014 | Ben-Yishai | G01B 11/002 |
| | | | | 356/614 |
| 2014/0225999 | A1* | 8/2014 | Bracke | A61B 34/10 |
| | | | | 348/77 |
| 2015/0342461 | A1* | 12/2015 | Ishikawa | A61B 5/7425 |
| | | | | 600/409 |
| 2019/0133695 | A1* | 5/2019 | Hladio | A61B 34/10 |
| 2019/0285397 | A1 | 9/2019 | Nakamura et al. | |

FOREIGN PATENT DOCUMENTS

| | | |
|---|---|---|
| JP | 2007-181564 | 7/2007 |
| JP | 2007-185491 | 7/2007 |
| JP | 4600735 | 10/2010 |
| JP | 2019-164109 | 9/2019 |

OTHER PUBLICATIONS

Maynard et al. "Device for Continuous Monitoring of Cerebral Activity in Resuscitated Patients", 1969, British Medical Journal (Year: 1969).*
"Input device", 2022, Wikipedia (Year: 2022).*
"VDU", 2009, techterms.com (Year: 2009).*
"Computer Monitor", 2022, Wikepedia (Year: 2022).*
"Fastrak Digitizer", 2018, Pohemus (Year: 2018).*

* cited by examiner

US 11,612,345 B2

INPUT DEVICE, MEASUREMENT SYSTEM, AND COMPUTER-READABLE MEDIUM

CROSS-REFERENCE TO RELATED APPLICATIONS

The present application claims priority under 35 U.S.C. § 119 to Japanese Patent Application No. 2018-048652, filed on Mar. 15, 2018 and Japanese Patent Application No. 2018-246035, filed on Dec. 27, 2018. The contents of which are incorporated herein by reference their entirety.

BACKGROUND OF THE INVENTION

1. Field of the Invention

The present invention relates to an input device, a measurement system, and a computer readable medium.

2. Description of the Related Art

Conventionally, in a magnetoencephalograph that measures magneto-encephalography (MEG), a feeble magnetic field that is generated in association with the brain activity (response of the brain to stimulation) is measured. By displaying the measured result on a magnetic resonance imaging (MRI) image of a subject in a superimposed manner, it is possible to find out at which region of the brain the activity occurred. In addition, in lieu of the measured magnetic field, by superimposing on the MRI image the generated position of current estimated based on the measured magnetic field, it makes it possible to learn the activity of the brain in more detail.

The coordinate system of the MRI image and the coordinate system of the MEG are different. In order to superimpose the measurement result of the magnetoencephalograph on the MRI image, the calculation of translation matrix between the coordinate systems is needed.

For this transformation matrix calculation, the coordinates of three points (fiducial point (FP)) of a nasion and left and right ears, which are reference points, are acquired on an MRI apparatus and the magnetoencephalograph. The following describes the respective methods of acquisition.

MRI apparatus: The above-described three points are specified on the image by a measurer.

Magnetoencephalograph: Marker coils (sensors) are attached to the above-described three points. In measuring, a magnetic field is generated from the marker coil (sensor) and the position of the marker coil (sensor) is measured by the magnetoencephalograph.

This allows the position of the FP to be obtained in the respective coordinate systems, and thus the transition matrix between the coordinate systems can be obtained.

In addition, in order to increase accuracy, disclosed has a technology that improves performance by acquiring the shape of an entire head, by acquiring the shape for which both the head and the magnetoencephalograph are put together when measuring, and by comparing those shapes (see Japanese Patent No. 4600735).

According to the conventional technology, because a majority of the head is hidden by a headpiece, positioning needs to be performed on a 3D image of a very small range. Furthermore, there has been a problem in that many of the exposed portions are areas where there is a concern of deformation (moving)) such as a jaw and, when deformed, it is not possible to correctly measure the positional relation between the brain that is a measurement target and the sensor.

Thus, according to the conventional technology, by using a digitizer that acquires the shape of a head by tracing the head with a tip of a stylus pen, the positional relation between the brain of the subject that is measurement target and the sensor is correctly measured.

Incidentally, when using a pen-type digitizer, in order to increase the accuracy in positioning, the coordinates of many points need to be collected in a well-balanced manner. For that purpose, according to the conventional technology, in a user interface of the digitizer, the already acquired points and the number thereof are displayed so as to let a user understand that a sufficient number of points is ensured and also data is acquired in all the range. Moreover, a screen that suggests an area to be traced with the stylus pen from now is also displayed.

However, there has been a problem in that the relation between the point plotted actually with the stylus pen of the digitizer and the area to be traced with the stylus pen from now is difficult to understand and the area to be traced next is difficult to understand.

SUMMARY OF THE INVENTION

According to an aspect of the present invention, an input device is to input a shape of a measurement target in response to a signal transmitted from a stylus pen, to determine positional relation between a position of a marker and a shape of the measurement target. The marker is attached to the measurement target and detectable by a cerebral-function measuring device. The input device includes a controller, and a display unit. The controller is configured to generate a screen in which a three-dimensional shape of the measurement target and a guide of a position to be acquired next with the stylus pen are superimposed. The display unit is configured to display the screen generated by the controller, on a display portion.

BRIEF DESCRIPTION OF THE DRAWINGS

The accompanying drawings are intended to depict exemplary embodiments of the present invention and should not be interpreted to limit the scope thereof. Identical or similar reference numerals designate identical or similar components throughout the various drawings.

DESCRIPTION OF THE EMBODIMENT

Figure 1:
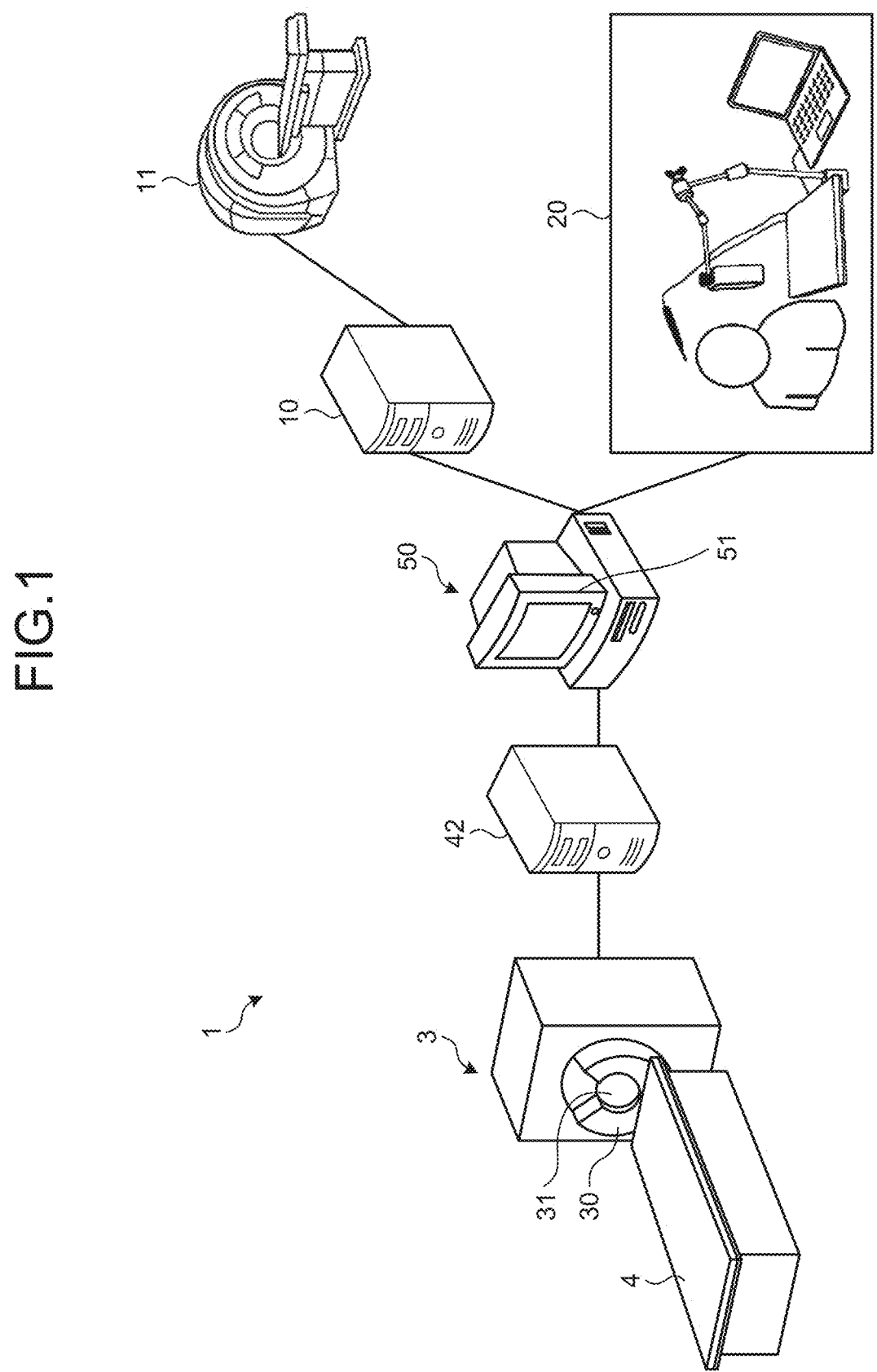
FIG. 1 is a schematic diagram of a biosignal measurement system according to an embodiment.

The terminology used herein is for the purpose of describing particular embodiments only and is not intended to be limiting of the present invention.

As used herein, the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

An embodiment of the present invention will be described in detail below with reference to the drawings.

An embodiment has an object to make it easy to understand the position to be acquired next with the stylus pen of the digitizer.

With reference to the accompanying drawings, the following describes in detail an exemplary embodiment of an input device, a measurement system, and a computer program.

FIG. 1 is a schematic diagram of a biosignal measurement system 1 according to the embodiment. The biosignal measurement system 1 measures and displays a plurality of types of biosignals, for example, a magneto-encephalography (MEG) signal and an electro-encephalography (EEG) signal.

As illustrated in FIG. 1, the biosignal measurement system 1 that is a measurement system includes a measuring device 3, a measurement table 4, a data recording server 42, and an information processing apparatus 50. The information processing apparatus 50 includes a monitor display 51 that displays signal information and analysis results obtained in measurement. In the present embodiment, the data recording server 42 and the information processing apparatus 50 are separately provided. However, at least a part of the data recording server 42 may be incorporated in the information processing apparatus 50.

The measuring device 3 is a cerebral-function measuring device and is a magnetoencephalograph that measures the MEG signal and the EEG signal. A subject who is a measurement target lies on his/her back on the measurement table 4, in a state in which electrodes (or sensors) for EEG measurement are attached to his/her head, and inserts the head to a hollow 31 of a dewar 30 of the measuring device 3. The dewar 30 is a container of cryogenic environment using liquid helium, and a number of magnetic sensors for MEG measurement are arranged inside the hollow 31 of the dewar 30. The measuring device 3 collects the EEG signals from the electrodes and the MEG signals from the magnetic sensors. The measuring device 3 outputs the collected biosignals to the data recording server 42.

In general, the dewar 30 having the built-in magnetic sensors and the measurement table 4 are arranged in a magnetic shield room. However, for the sake of convenience of illustration, the magnetic shield room is omitted.

The data recording server 42 records data such as the biosignals output from the measuring device 3.

The information processing apparatus 50 reads out the data recorded in the data recording server 42, and displays the data on the monitor display 51 and also analyzes it. The information processing apparatus 50 displays waveforms of the MEG signals from the magnetic sensors and waveforms of the EEG signals from the electrodes, in synchronization on the same time axis. The EEG signal represents electrical activities of nerve cells (flow of ionic charges that occurs at dendrites of neurons in synaptic transmission) as a voltage value between electrodes. The MEG signal represents minute magnetic field variations that are caused by electrical activities of the brain. The brain magnetic field is detected by a superconducting quantum interference device (SQUID) sensor of high sensitivity.

In addition, the biosignal measurement system includes a biological-image measurement apparatus 11, and a biological-image recording server 10 to which the biological-image measurement apparatus 11 is coupled. The biological-image recording server 10 is coupled to the information processing apparatus 50. The biological-image measurement apparatus 11 is an MRI apparatus that images a magnetic resonance imaging (MRI) image of the subject who is a measurement target. The biological-image recording server 10 stores therein the MRI image imaged by the biological-image measurement apparatus 11.

Figure 2:
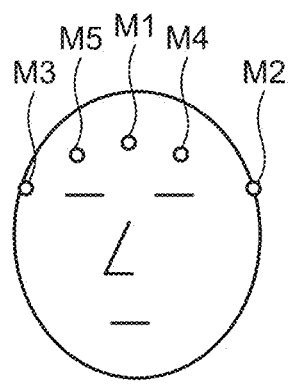
FIG. 2 is a diagram illustrating a head of a subject who is a measurement target.

FIG. 2 is a diagram illustrating a head of the subject who is a measurement target. As illustrated in FIG. 2, on the head of the subject who is a measurement target, marker coils M1, M2, M3, M4, and M5 that are fiducial points (FPs) are attached. In more detail, the marker coil M1 is attached to a nasion, the marker coils M2 and M3 are respectively attached to the left and right ears, and the marker coils M4 and M5 are respectively attached to the forehead on the left and right interposing the nasion.

The measuring device 3 measures, in measuring, the position of the marker coil on the basis of the magnetic field generated from the marker coil. Meanwhile, in the biological-image measurement apparatus 11, a measurer specifies the FP on the image. This allows the position of the FP to be obtained in the respective coordinate systems, and thus the translation matrix between the coordinate systems can be obtained.

In addition, the biosignal measurement system 1 includes a three-dimensional digitizer 20 that is an input device. The three-dimensional digitizer 20 is coupled to the information processing apparatus 50. The biosignal measurement system 1, by using the three-dimensional digitizer 20, correctly measures the positional relation between the brain of the subject that is a measurement target and the sensor. The three-dimensional digitizer 20 measures the head shape of the subject that is a measurement target, and the attached positions of the marker coils M1, M2, M3, M4, and M5 for detecting the head position in the measuring device 3.

Next, the three-dimensional digitizer 20 will be described.

Figure 3:
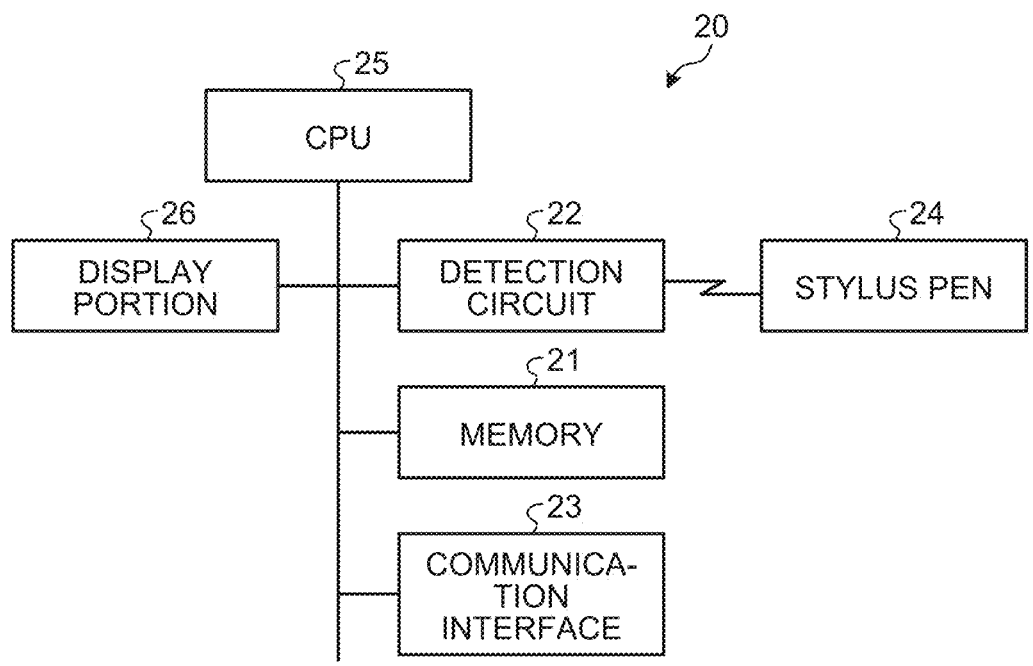
FIG. 3 is a block diagram illustrating a hardware configuration of a three-dimensional digitizer.

FIG. 3 is a block diagram illustrating a hardware configuration of the three-dimensional digitizer 20. As illustrated in FIG. 3, the three-dimensional digitizer 20 incorporates a central processing unit (CPU) 25 that controls the whole of the three-dimensional digitizer 20. The CPU 25 built into the three-dimensional digitizer 20 is coupled to a detection circuit 22 that detects the position of a stylus pen 24, a memory 21, a communication interface 23, and a display portion 26 that is a liquid crystal display (LCD). The stylus pen 24 is a pen that emits an electromagnetic field or detects an electromagnetic field, and when sensed the contact with the head of the subject that is a measurement target, the coordinate of the tip position of the stylus pen is detected by the detection circuit 22. The coordinate may be acquired at the timing of depressing a coordinate acquisition button (built into the stylus pen 24, or provided outside via wireless connection), or the coordinate may be acquired continuously for a certain period of time.

The memory 21 is composed of a large capacity flash memory or a hard disk, and the coordinate of a writing position is stored in a rewritable state. Meanwhile, the communication interface 23 is composed of a USP port or the like.

The memory 21 stores therein various control programs. For example, the CPU 25 executes the various control programs stored in the memory 21 and outputs control commands for controlling various operations in the three-dimensional digitizer 20.

The control programs that the CPU 25 of the three-dimensional digitizer 20 in the present embodiment executes may be recorded and provided in a file of an installable or executable format on a computer-readable recording medium such as a CD-ROM, a flexible disk (FD), a CD-R, and a digital versatile disc (DVD).

Moreover, the control programs that the CPU 25 of the three-dimensional digitizer 20 in the present embodiment executes may be stored in a computer connected to a network such as the Internet and be provided by being downloaded via the network. The control programs that the CPU 25 of the three-dimensional digitizer 20 in the present embodiment executes may provided or distributed via a network such as the Internet.

Next, the functions of the three-dimensional digitizer 20 exercised as the CPU 25 executes the various control programs stored in the memory 21 will be described. The description of functions conventionally known is omitted, and characteristic functions exercised by the three-dimensional digitizer 20 of the present embodiment will described in detail.

Figure 4:
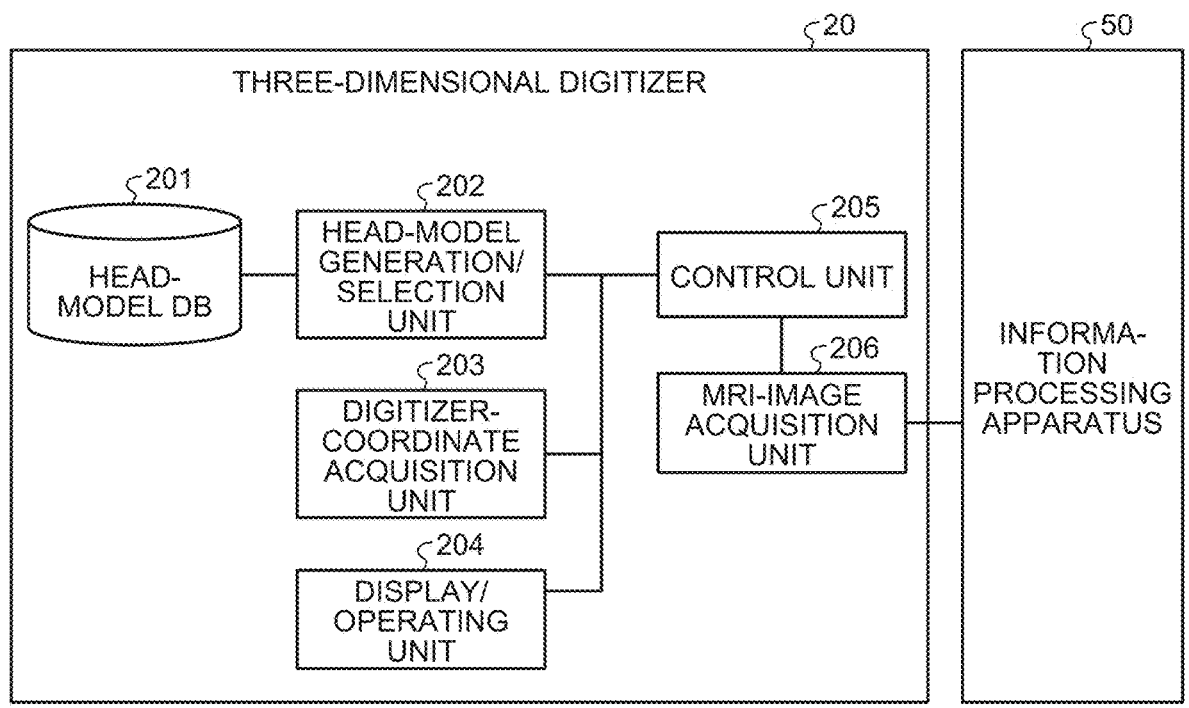
FIG. 4 is a functional block diagram illustrating functions of the three-dimensional digitizer.

FIG. 4 is a functional block diagram illustrating the functions of the three-dimensional digitizer 20. As illustrated in FIG. 4, the three-dimensional digitizer 20 includes a head-model DB 201, a head-model generation/selection unit 202 that is a model acquisition unit, a digitizer-coordinate acquisition unit 203, a display/operating unit 204 that is a display unit, a controller 205 that is a control unit, and an MRI-image acquisition unit 206.

The control unit 205 receives signals from the various units (the head-model generation/selection unit 202, the digitizer-coordinate acquisition unit 203, the display/operating unit 204, and the MRI-image acquisition unit 206) and transmits appropriate commands.

The digitizer-coordinate acquisition unit 203 acquires the position coordinate of a pen point of the stylus pen 24.

The display unit 204 acquires the operation of the user via a mouse and the like and sends it to the control unit 205, and also performs display corresponding to the command from the control unit 205 on the display portion 26.

The MRI-image acquisition unit 206 acquires, by the commands from the control unit 205, the MRI image of the subject imaged by the biological-image measurement apparatus 11 from the biological-image recording server 10 via the information processing apparatus 50.

The head-model DB 201 stores therein 3D head shape models. It does not matter even if the 3D head shape model is an image that is acquired actually, or a 3D model that is artificially generated. As the simplest form, a model for which protrusions representing a nose and ears are provided on a sphere will do. In the present embodiment, it is stored in a state in which three FPs (the marker coil M1 of a nasion, and the marker coils M2 and M3 of left and right ears: nasion, left ear, and right ear) are set with respect to the 3D head shape model.

The head-model generation/selection unit 202 performs any, of the following processing.

First, the head-model generation/selection unit 202 selects, out of the 3D head shape models stored in the head-model DB 201, a 3D head shape model to which the arrangement of the three FPs is the most analogous.

In more detail, the head-model DB 201 stores therein a large number of 3D head shape models different in race and age. The head-model generation/selection unit 202, when it is received that three FPs were specified the stylus pen 24 via the digitizer-coordinate acquisition unit 203, selects the model to which the arrangement of the three FPs is the most analogous out of the 3D head shape models stored in the head-model DB 201, and displays a screen on the display portion 26 via the display/operating unit 204.

Figure 5:
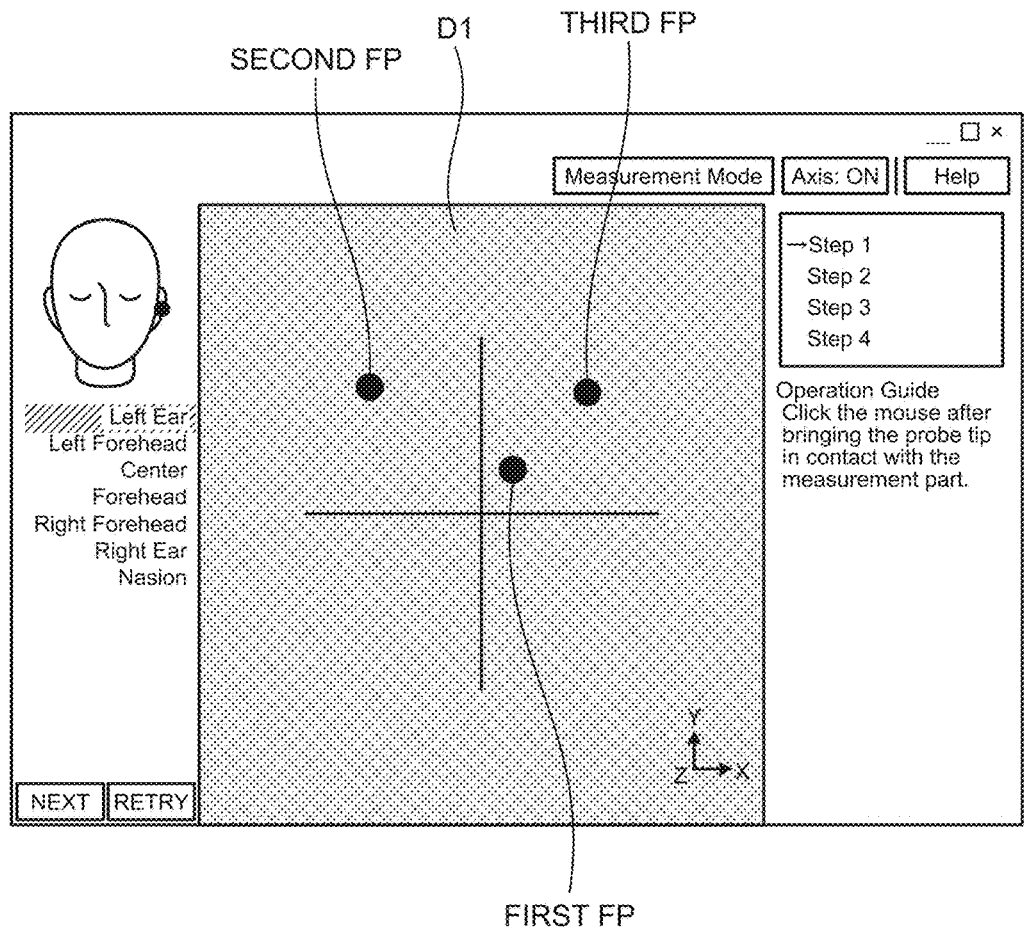
FIG. 5 is a diagram illustrating an example of specifying three FPs on a screen.
Figure 6:
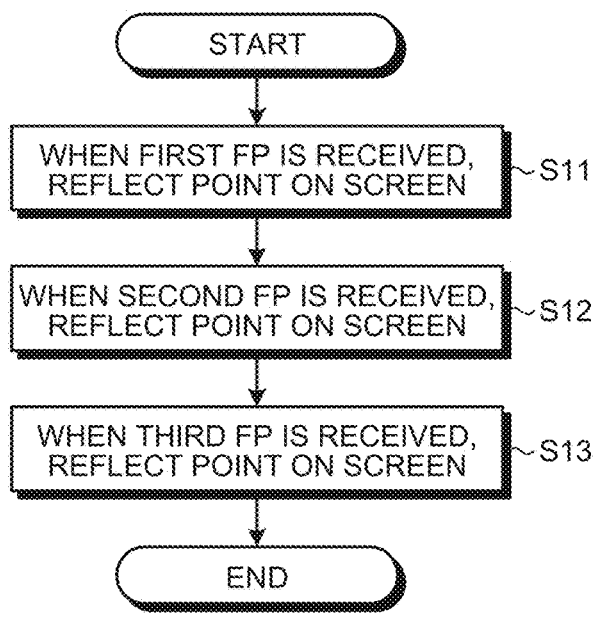
FIG. 6 is a flowchart illustrating a processing flow of specifying three FPs.

Specifying three FPs will be described simply. FIG. 5 is a diagram illustrating an example of specifying three FPs on a screen D1, and FIG. 6 is a flowchart illustrating a processing flow of specifying the three FPs. When the three-dimensional digitizer 20 is started up and the first FP specified with the stylus pen 24 is received, the head-model generation/selection unit 202 reflects and displays the first point on the screen D1 (Step S11). Similarly, when the second FP specified with the stylus pen 24 is received, the head-model generation/selection unit 202 reflects and displays the second point on the screen D1 (Step S12). When the third FP specified with the stylus pen 24 is received, the head-model generation/selection unlit 202 reflects and displays the third point on the screen D1 (S13). As just described, the three FPs are determined.

The 3D head shape model does not necessarily need to be artificial, and by storing a great number of MRI images in the head-model DB 201, a model analogous to the subject from the three FPs may be selected. However, in that case, it is preferable to make it possible to understand that, on the screen, the selected 3D head shape model is not that of the subject himself/herself.

Second, the head-model generation/selection unit 202 deforms, on the 3D head shape model stored in the head-model DB 201, the arrangement of three FPs so as to be the same as that of the three FPs specified with the stylus pen 24.

In more detail, the head-model DB 201 stores therein one 3D head shape model. The head-model generation/selection unit 202, when it is received that three FPs were specified with the stylus pen 24 via the digitizer-coordinate acquisition unit 203, deforms the 3D head shape model stored in the head-model DB 201 so as to match the coordinates of the three FPs specified with the us pen 24, and displays the screen on the display portion 26 via the display/operating unit 204.

Figure 7:
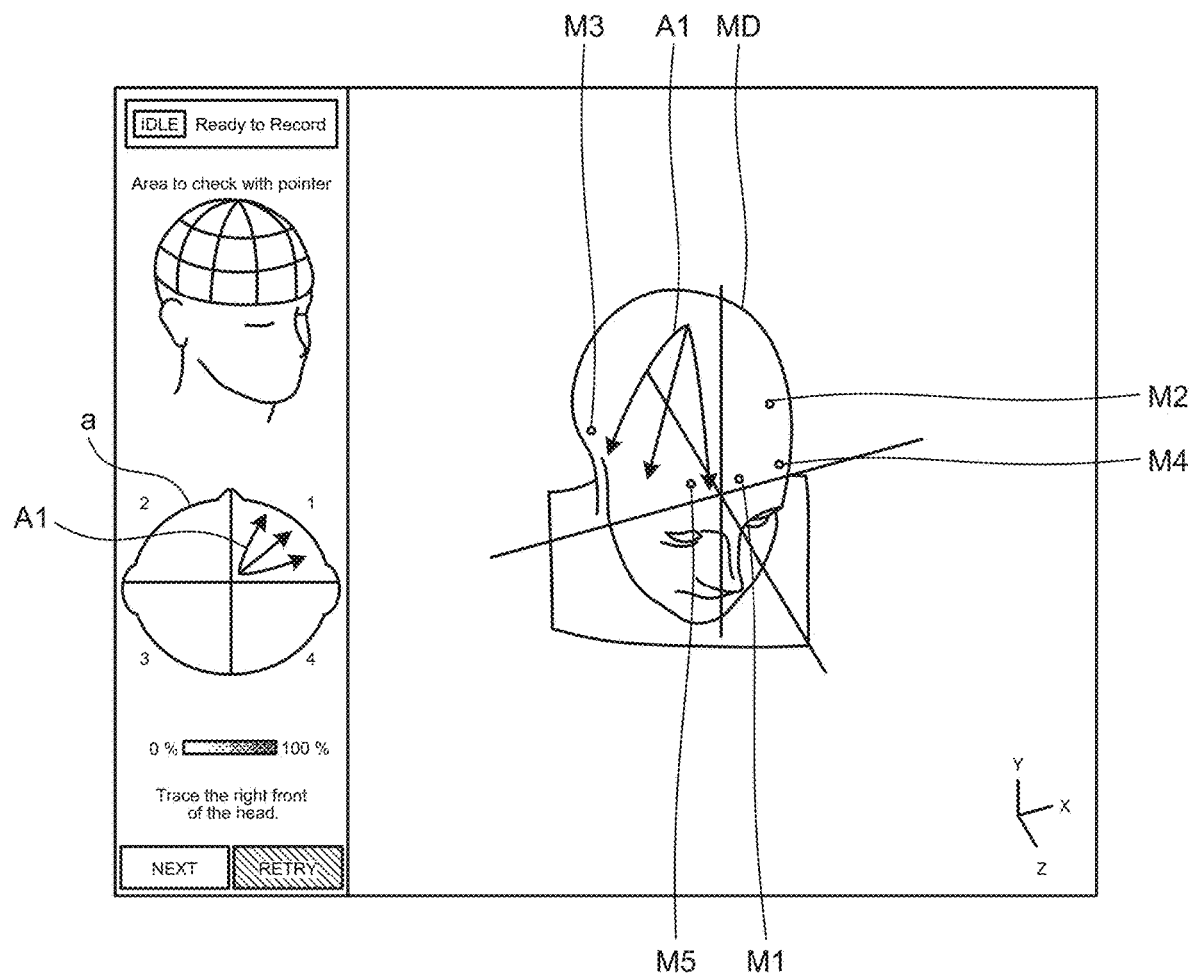
FIG. 7 is a diagram illustrating one example of a UI image displayed on a display portion of the three-dimensional digitizer.
Figure 8:
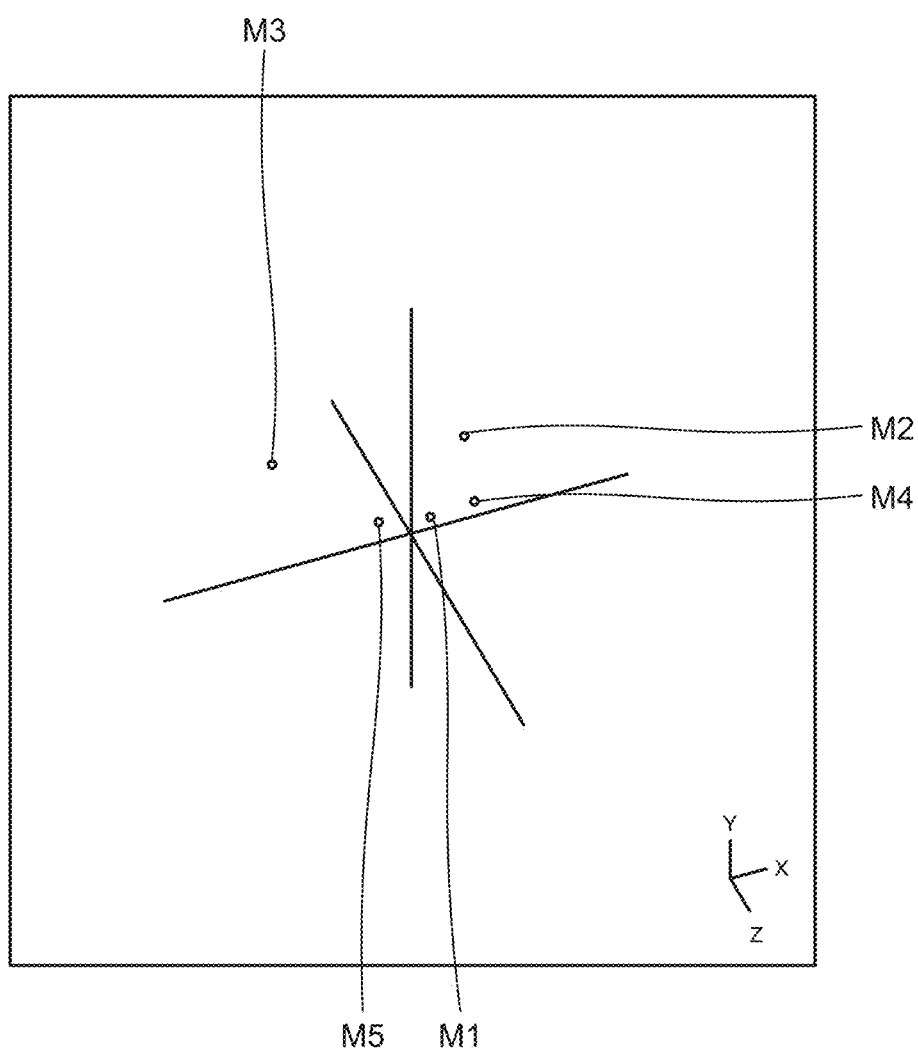
FIG. 8 is a diagram illustrating one example of a UI image displayed on a display portion of a conventional three-dimensional digitizer.

FIG. 7 is a diagram illustrating one example of a user interface (UI) image displayed on the display portion 26 of the three-dimensional digitizer 20, and FIG. 8 is a diagram illustrating one example of a UI image displayed on a display portion of a conventional three-dimensional digitizer. As illustrated in FIG. 7, the control unit 205 of the three-dimensional digitizer 20 displays in a superimposed manner an area (a guide of the position to be acquired next) A1 to be traced with the stylus pen 24 from now and a 3D head shape model MD selected in the head-model generation/selection unit 202. As just described, by displaying in a superimposed manner the area A1 to be traced with the stylus pen 24 from now and the 3D head shape model MD, as compared with the UI image displayed on the display portion of the conventional three-dimensional digitizer illustrated in FIG. 8, the relation between the points plotted actually with the stylus pen 24 of the three-dimensional digitizer 20 and the area to be traced with the stylus pen 24 from now is easy to understand. This enables the user to understand intuitively which data to acquire next with the stylus pen 24 of the three-dimensional digitizer 20.

The reference sign as illustrated in FIG. 7 is a planar image of the head shape model. In this way, by displaying the planar image a of the head shape model, it makes it easy to visually recognize the area A1 of the depth direction that is difficult to understand with the 3D head shape model MD.

The generation of the area A1 a guide of the position to be acquired next) to be traced with the stylus pen 24 from now plublicly known, and thus the description thereof is omitted.

As in the foregoing, the head shape is different by means of race and age and is in a variety of shapes. Thus, when simply one head shape model is displayed, the display of the actually acquired points and the guide of the point to acquire next may be displayed being greatly displaced, and that may be misleading.

Consequently, in the three-dimensional digitizer 20 of the present embodiment, the 3D held shape model MD analogous to the subject is prepared by either of the above-described two methods and the area A1 to be traced with the stylus pen 24 from now is displayed on the UI image in a superimposed manner.

Next, the processing of displaying UI image in the three-dimensional digitizer 20 will be described.

Figure 9:
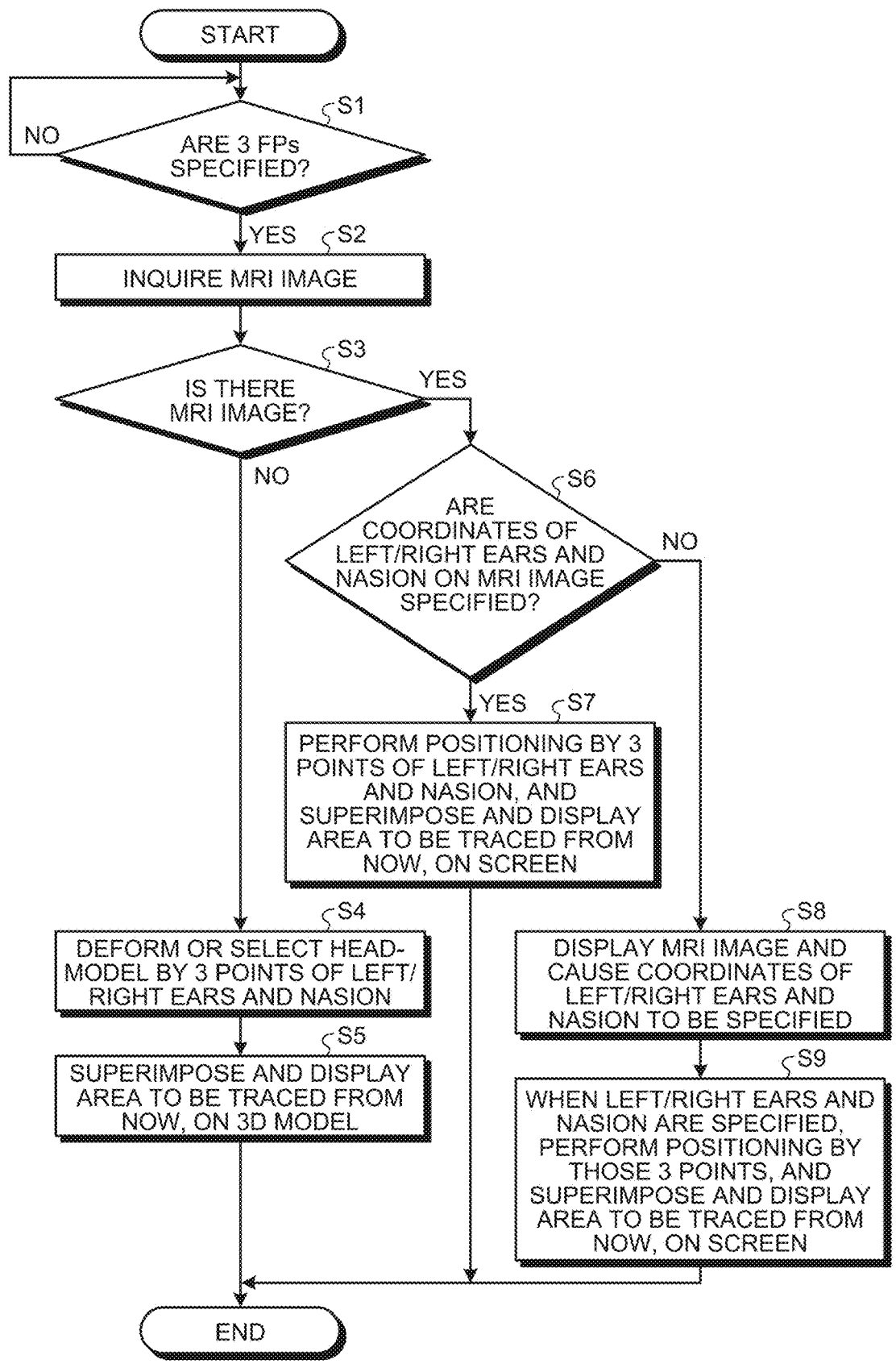
FIG. 9 is a flowchart schematically illustrating a processing flow of displaying the UI image.

FIG. 9 is a flowchart schematically illustrating a processing flow of displaying the UI image.

As illustrated in FIG. 9, when it is received that the three FPs (nasion, left ear, and right ear) were specified with the stylus pen 24 via the digitizer-coordinate acquisition unit 203 (Yes, at Step S1), the control unit 205 inquires of the MRI-image acquisition unit 206 in order to acquire the MRI image of the subject imaged by the biological-image measurement apparatus 11 (Step S2).

The fact that the FP was specified with the stylus pen 24 means bringing the pen point into contact with the FP and acquiring the coordinate by pressing a switch of some sort. Examples of the switch include a switch for which the pen point is the switch, a switch that is pressed down by hand other than the hand holding the stylus pen 24, and the like.

There may be a case where it is not possible to acquire the MRI image when the measurement of MEG by the measuring device 3 that is the magnetoencephalograph is preceded or the like. The control unit 205 advances, if it is possible to acquire the MRI image (Yes, at. Step S3), to Step S6 and, if it is not possible to acquire the MRI image (No, at Step S3), advances the processing to Step S4.

At Step S6, the control unit 205 confirms whether the coordinates of the three FPs (nasion, left ear, and right ear) have already been specified on the acquired MRI image (3D image) of the subject. Even if the coordinates of the three FPs (nasion, left ear, and right ear) are in the header of the MRI image, or in a file separate from the MRI image, the method of management is not concerned.

The control unit 205 advances, if the coordinates of the three FPs (nasion, left ear, and right ear) have already been specified on the MRI image of the subject (Yes at Step S6), to Step 7 and, the coordinates of the three FPs (nasion, left ear, and right ear) have not been specified on the MRI image of the subject (No, at Step S6), advances to Step S8.

At Step S7, the control unit 205 enlarges, reduces, rotates, and deforms the MRI image acquired from the MRI-image acquisition unit 206 for positioning to match the three points of FPs (nasion, left ear, and right ear), and displays it on the display portion 26 by superimposing the area A1 to be traced with the stylus pen 24 from now via the display/operating unit 204.

Figure 10:
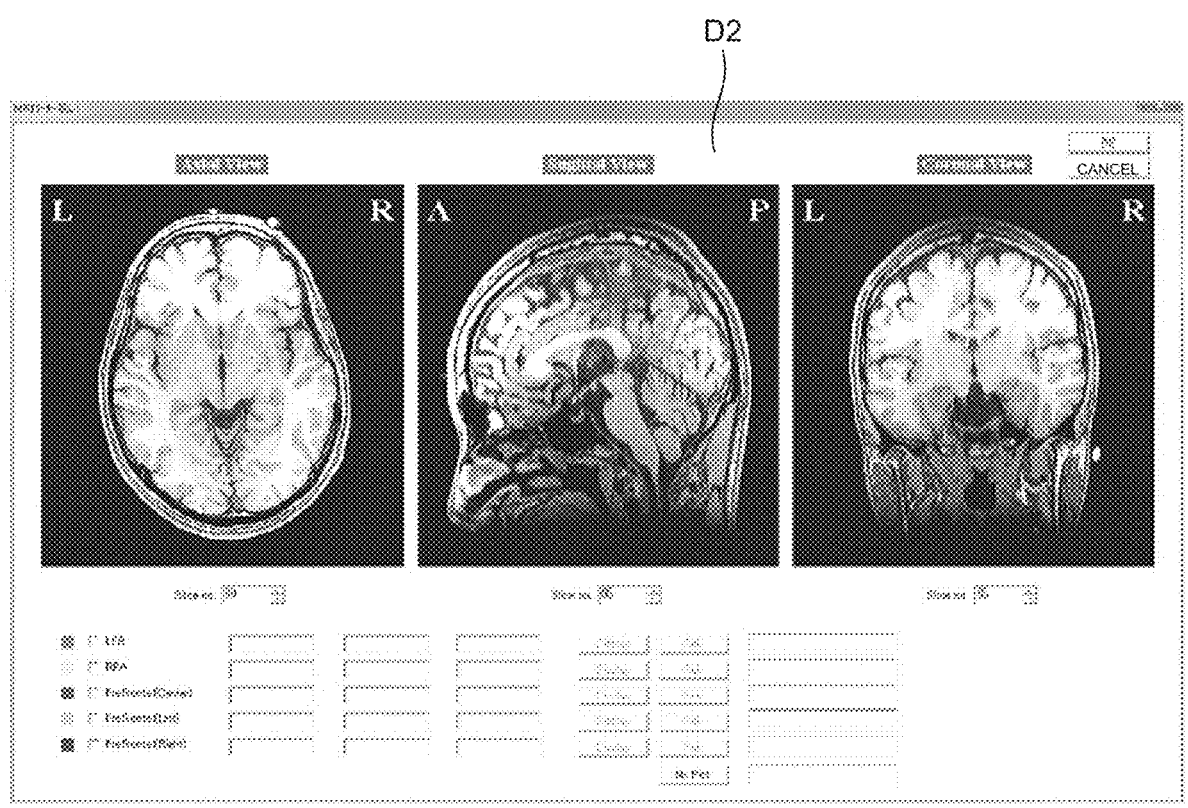
FIG. 10 is a diagram illustrating a user interface in which three FPs are specified on MRI images.

At Step S8, the control unit 205 displays the MRI image acquired from the MRI-image acquisition unit 206 on the display portion 26 via the display/operating unit 204 and lets the user specify the three FPs (nasion, left ear, and right ear). FIG. 10 is a diagram illustrating a user interface in which three FPs are specified on MRI images D2.

The control unit 205 performs, at the time the three FPs (nasion, left ear, and right ear) were specified (for example, at the time the nasion was specified), the positioning on the MRI image acquired from the MRI-image acquisition unit 206 with these three points, and via the display/operating unit 204, displays it on the display portion 26 by superimposing the area A1 to be traced with the stylus pen 24 from now (Step S9).

Meanwhile, at S4, the head-model generation/selection unit 202 selects from the head-model DB 201 a 3D head shape model matching the three FPs (nasion, left ear, and right ear) specified with the stylus pen 24, or deforms a 3D head shape model so as to match the three FPs (nasion, left ear, and right ear) specified with the stylus pen 24.

Thereafter, the control unit 205 makes the three FPs (nasion, left ear, and right ear) of the selected or deformed 3D head shape model MD coincide width the currently specified three FPs (nasion, left ear, and right ear), and displays it on the display portion 26 by superimposing on the 3D model MD the area A1 to be traced with the stylus pen 24 from now via the display/operating unit 204 (Step S5).

Figure 11:
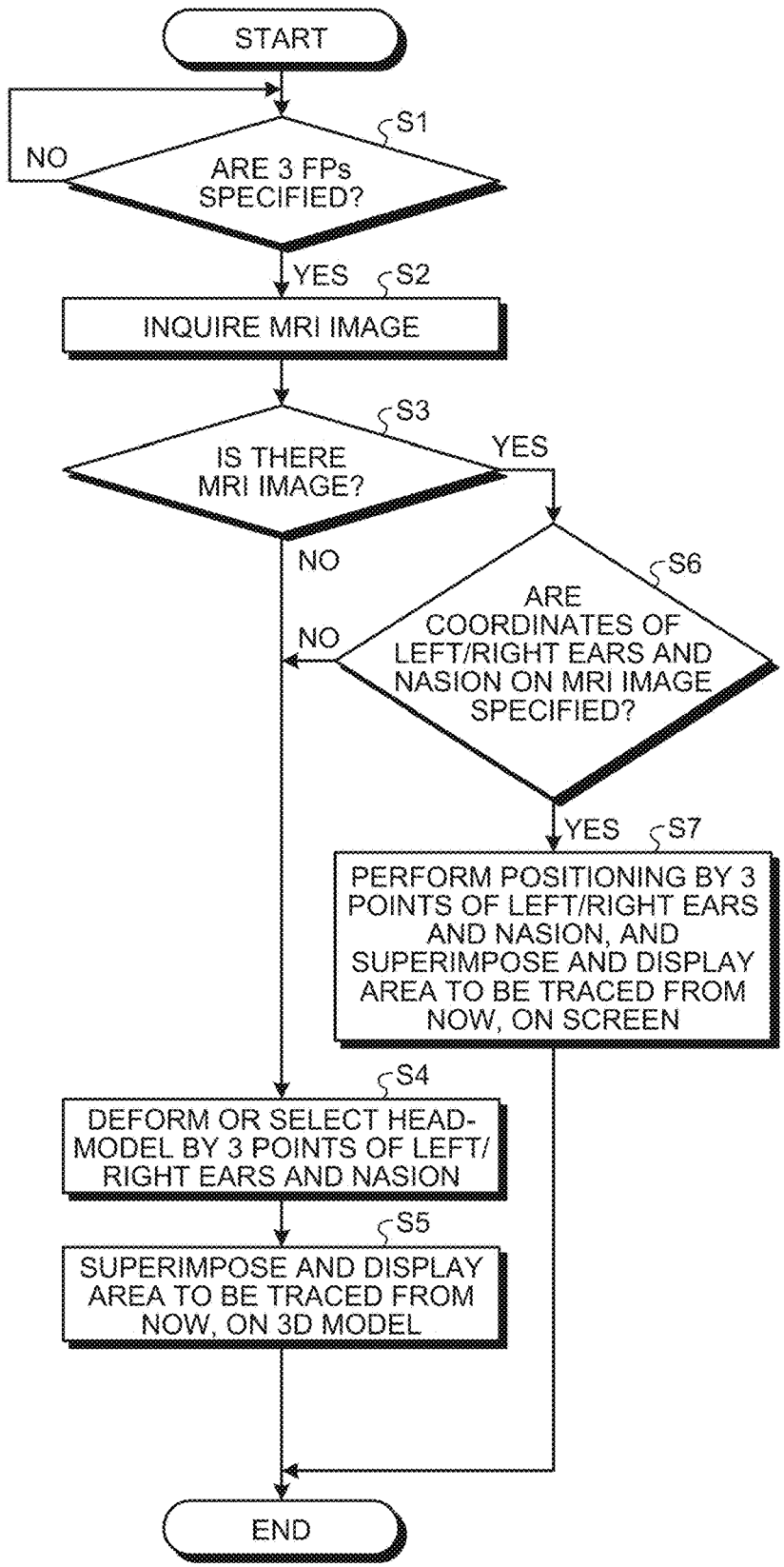
FIG. 11 is a modification of the flowchart schematically illustrating the processing flow of displaying the UI image.

In the flowchart illustrated in FIG. 9, although the coordinate has been specified (Step S8), the embodiment is not limited thereto. FIG. 11 is a modification of the flowchart schematically illustrating the processing flow of displaying the UI image.

As illustrated in FIG. 11, if the coordinates of the three FPs (nasion, left ear, and right ear) are not specified on the MRI image of the subject (No, at Step S6), the processing is advanced to Step S4, and the head-model generation/selection unit 202 either selects from the head-model DB 201 a 3D head shape model matching the three FPs (nasion, left ear, and right ear) specified with the stylus pen 24 or deforms a 3D head shape model so as to match the three FPs (nasion, left ear, and right ear) specified with the stylus pen 24.

Thus, even if there is an MRI image of the subject, when not specified on the MRI image, the use of not the coordinate specified on the MRI image but a head model has an advantage in that it does not cause a trouble of the measurer.

Figure 12:
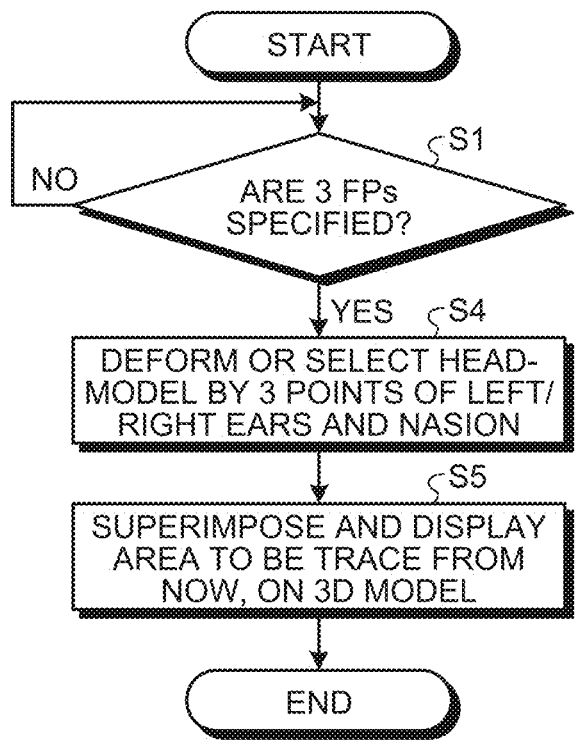
FIG. 12 is a modification of the flowchart schematically illustrating the processing flow of displaying the UI image.

In the flowchart illustrated in FIG. 9, although the presence of the MRI image has been confirmed, the embodiment is not limited thereto and a head model may be used, without confirming the presence of the MRI image. FIG. 12 is a modification of the flowchart schematically illustrating the processing flow of displaying the UI image.

As illustrated in FIG. 12, if it is received that the three FPs (nasion, left ear, and right ear) were specified with the stylus pen 24 via the digitizer-coordinate acquisition unit 203 (Yes, at Step S1), the processing is advanced to Step S4 and the head-model generation/selection unit 202 either selects, from the head-model DB 201, a 3D head shape model matching the three FPs (nasion, left ear, and right ear) specified with the stylus pen 24 or deforms 3D head shape model so as to match with the three FPs (nasion, left ear, and right ear) specified with the stylus pen 24.

This makes the confirmation of the MRI image unnecessary, and has an advantage in that the processing becomes simple and it does not cause a trouble of the measurer.

It is also possible to make the 3D head shape model erect or make it face the front, by using the information on the top and bottom of the MRI image, at the time the three FPs left ear, and right ear) were superimposed. This makes it possible to deal with when the directions of top and bottom, left and right, and front and rear are indeterminate, at an initial state, depending on the model of the three-dimensional digitizer 20.

In addition, in order to make it easy to see on the screen the area to be traced with the stylus pen 24 from now, performing the following contrivances is suggested. First, the control unit 205 rotates the coordinate system (the 3D head shape model, and the points that have been collected already) such that the area to be traced with the stylus pen 24 from now is located front. Second, the control unit 205 performs 3D display with the viewpoint placed at the position of the stylus pen 24.

As in the foregoing, according to the present embodiment, when there is an MRI image, the area A1 to be traced from now is displayed in a superimposed manner after making the MRI image into an appropriate form, and when there is no MRI image, the area A1 to be traced from now is displayed in a superimposed manner after making a prepared 3D head model into an appropriate form, and the operation of the stylus pen 24 of the three-dimensional digitizer 20 is guided. Thus, the positioning between the MRI coordinate system and the MEG coordinate system can be performed by intuitive easy-to-understand operation without regard for the acquisition of the MRI image. Furthermore, it facilitates intuitive understanding of the points that have been specified by the three-dimensional digitizer 20 and the point to specify next with the stylus pen 24 of the three-dimensional digitizer 20.

Modifications

Modifications of the present embodiment will be described.

The three-dimensional digitizer 20 of the present embodiment is able to acquire the position of the stylus pen 24 that traces the head even when the stylus pen 24 is not brought into contact with the head. Accordingly, the control unit 205 may display the pen point position of the stylus pen 24 on the screen. Furthermore, in order to guide the operation of the stylus pen 24, the control unit 205 may display the pen point position of the stylus pen 24 on the screen and the direction to which the stylus pen 24 moves may be indicated by an arrow and the like.

Figure 13:
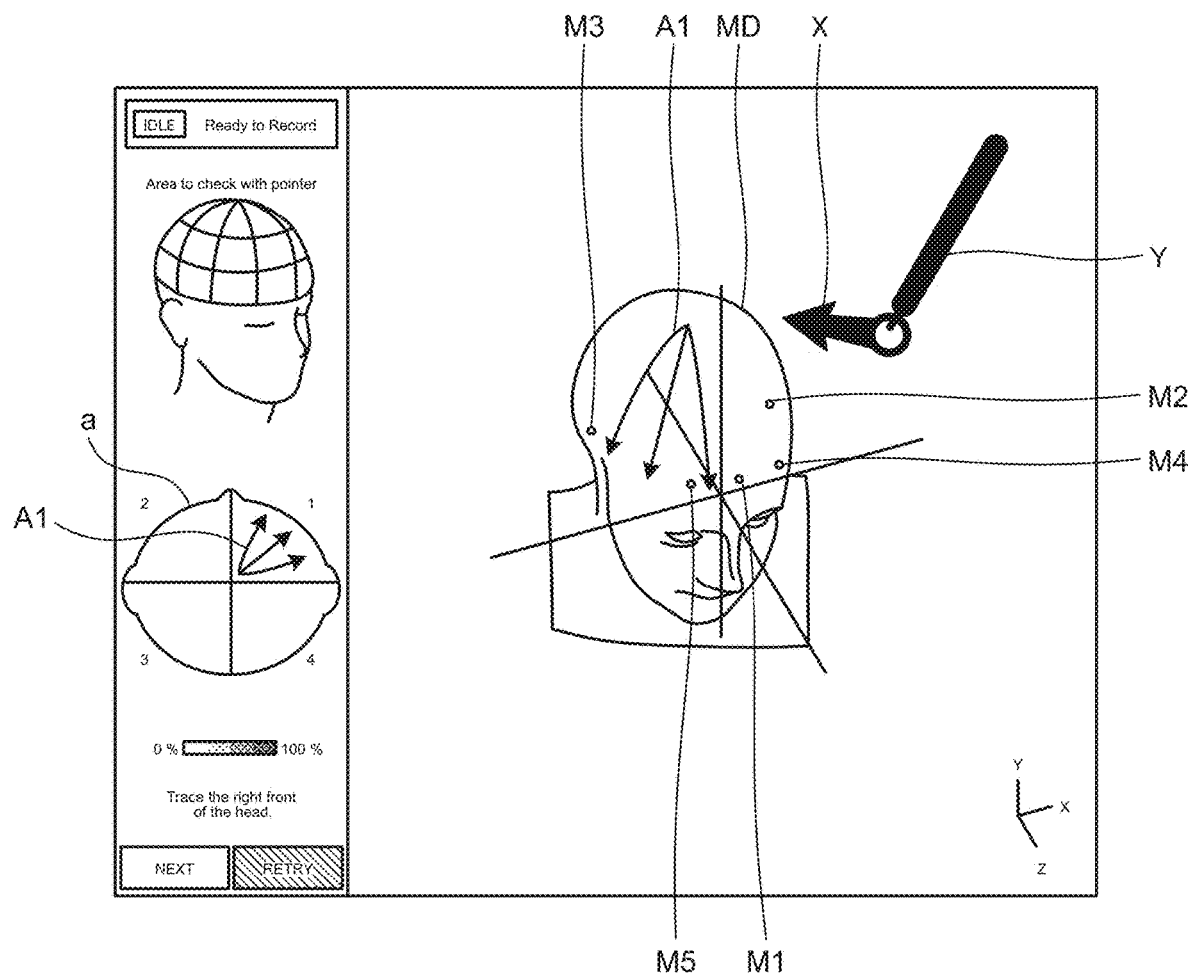
FIG. 13 is a diagram illustrating a modification of the screen.

FIG. 13 is a diagram illustrating a modification of the screen. According to the screen example illustrated in FIG. 13, a pen point position Y of the stylus pen 24 is displayed and also the direction to which the stylus pen 24 moves is indicated by an arrow X. Thus, is possible to indicate the moving direction of the stylus pen 24 toward an appropriate position of the area to be traced with the stylus pen 24 from now with respect to the head.

Figure 14:
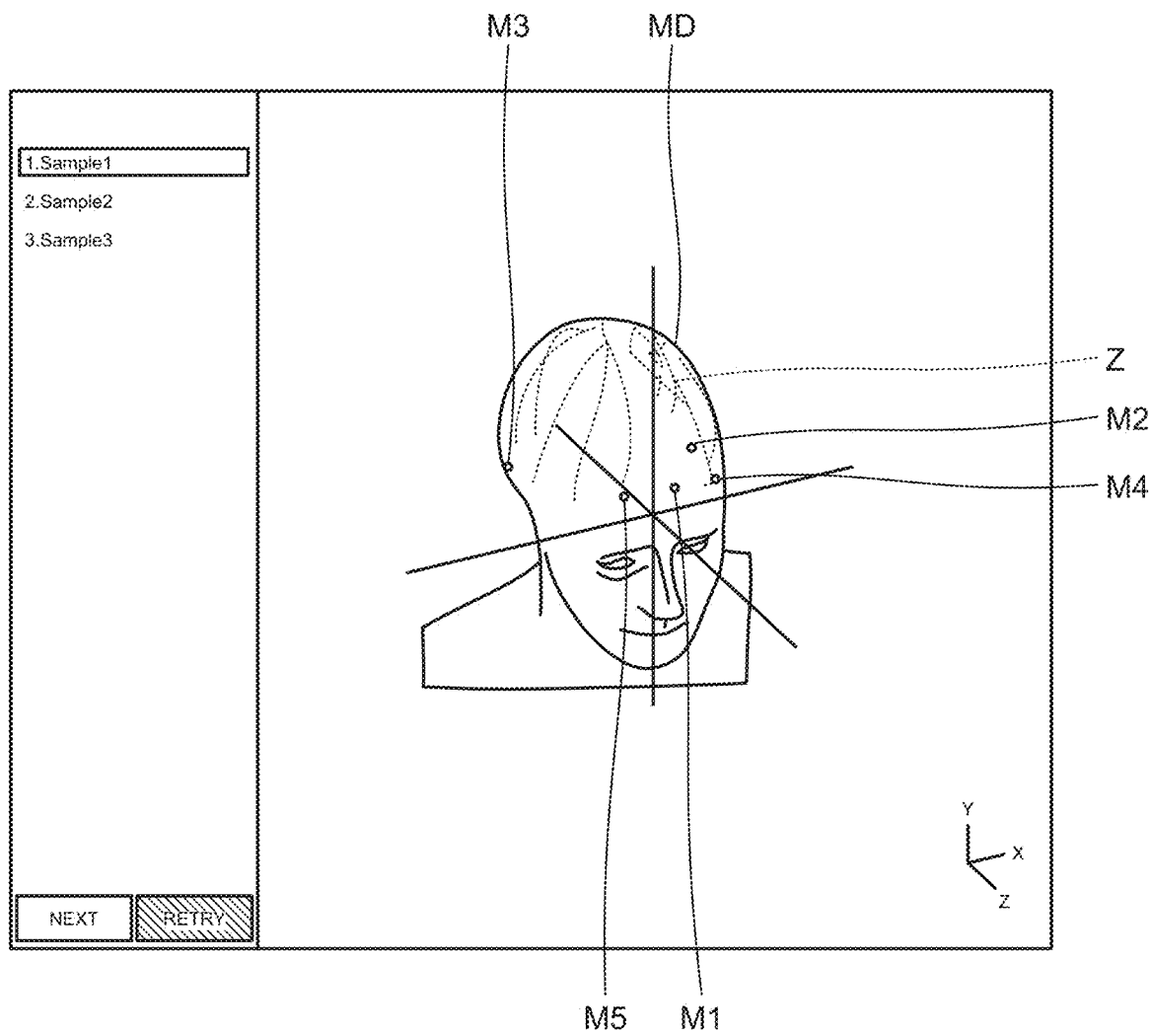
FIG. 14 is a diagram illustrating another modification of the screen.

FIG. 14 is a diagram illustrating another modification of the screen. According to the screen example illustrated in FIG. 14, the control unit 205 further displays trajectories Z that have already been traced with the stylus pen 24 with respect to the head.

An embodiment provides an advantageous effect that it is possible to make it easy to understand the position to be acquired next with the stylus pen of the digitizer.

The above-described embodiments are illustrative and do not limit the present invention. Thus, numerous additional modifications and variations are possible in light of the above teachings. For example, at least one element of different illustrative and exemplary embodiments herein may be combined with each other or substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of the present invention may be practiced otherwise than as specifically described herein.

The method steps, processes, or operations described herein are not to be construed as necessarily requiring their performance in the particular order discussed or illustrated, unless specifically identified as an order of performance or clearly identified through the context. It is also to be understood that additional or alternative steps may be employed.

Further, any of the above-described apparatus, devices or units can be implemented as a hardware apparatus, such as a special-purpose circuit or device, or as a hardware/software combination, such as a processor executing a software program.

Further, as described above, any one of the above-described and other methods of the present invention may be embodied in the form of a computer program stored in any kind of storage medium. Examples of storage mediums include, but are not limited to, flexible disk, hard disk, optical discs, magneto-optical discs, magnetic tapes, non-volatile memory, semiconductor memory, read-only-memory (ROM), etc.

Alternatively, any one of the above-described and other methods of the present invention may be implemented by an application specific integrated circuit (ASIC), digital signal processor (DSP) or a field programmable gate array (FPGA), prepared by interconnecting an appropriate network of conventional component circuits or by a combination thereof with one or more conventional general purpose microprocessors or signal processors programmed accordingly.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA) and conventional circuit components arranged to perform the recited functions.

What is claimed is:

1. An input device comprising:
   a controller configured to,
   receive a first signal transmitted from a stylus pen, the first signal including position information of at least three markers adapted to be attached to a measurement target, the position information corresponding to a first shape of the measurement target, the at least three markers corresponding to fiducial points of the measurement target, determine positional relationship between positions of the at least three markers and the first shape of the measurement target based on the position information, the at least three markers being detectable by a cerebral-function measuring device, generate a screen in which a second shape of the measurement target and a guide of a position to be acquired next with the stylus pen are superimposed, the second shape of the measurement target being a three-dimensional (3D) shape of the measurement target generated based on the determined positional relationship between the positions of the at least three markers and the first shape of the measurement target, the guide of the position to be acquired next being a line to be traced next along the measurement target using the stylus pen, the line to be traced next not connected to and not comprising the fiducial points of the measurement target and tracing the first shape of the measurement target, and receive a second signal transmitted from the stylus pen as the stylus pen is moved along the line to be traced next, the second signal continuously providing position information of the stylus pen, wherein the stylus pen is configured to be in direct contact with the measurement target as the second signal is transmitted; and a display unit configured to display the generated screen.

2. The input device according to claim 1, wherein the controller is further configured to:

acquire a 3D model of the first shape of the measurement target; and use the 3D model of the first shape of the measurement target as the second shape of the measurement target.

3. The input device according to claim 2, wherein the fiducial points include at least three fiducial points; and the controller is further configured to generate the 3D model of the first shape of the measurement target by, altering the acquired 3D model based on the at least three fiducial points.

4. The input device according to claim 2, wherein the fiducial points include at least three fiducial points; and the controller is further configured to acquire the 3D model of the first shape of the measurement target by, selecting a model from a plurality of 3D models corresponding to a same type as the measurement target based on an arrangement of the at least three fiducial points.

5. The input device according to claim 1, wherein the controller is further configured to use a measurement image of the measurement target obtained from a medical imaging apparatus as the second shape of the measurement target.

6. The input device according to claim 1, wherein the controller is further configured to rotate a coordinate system associated with the cerebral-function measuring device such that the guide of the position to be acquired next with the stylus pen is located to a front position of the coordinate system.

7. The input device according to claim 1, wherein the controller is further configured to change a view of the 3D shape of the measurement target in response to a change in orientation of the stylus pen.

8. The input device according to claim 1, wherein the controller is further configured to further include a current position of the stylus pen on the generated screen.

9. The input device according to claim 1, wherein the controller is further configured to display the generated screen by:

displaying at least one line corresponding to the second signal on the second shape of the measurement target.

10. The input device according to claim 5, wherein the medical imaging apparatus is a magnetic resonance imaging (MRI) device; and the second shape of the measurement target is a 3D MRI image of the measurement target obtained by the MRI device.

11. The input device according to claim 10, wherein the controller is further configured to:

alter the 3D MRI image of the measurement target based on the position information received from the stylus pen.

12. The input device according to claim 10, wherein the controller is further configured to:

translate a coordinate system corresponding to the MRI device to a coordinate system corresponding to the cerebral-function measuring device.

13. The input device according to claim 8, wherein the controller is further configured to further display, on the generated screen, a direction in which the stylus pen is to move.

14. A measurement system comprising:

a cerebral-function measuring device configured to detect at least three markers adapted to be attached to a measurement target, the at least three markers corresponding to fiducial points of the measurement target;

a stylus pen configured to transmit a first signal, the first signal including position information corresponding to a first shape of the measurement target; and an input device configured to, receive the first signal transmitted by the stylus pen, determine positional relationship between the position of the at least three markers and the first shape of the measurement target based on the position information, generate a screen in which a second shape of the measurement target and a guide of a position to be acquired next with the stylus pen are superimposed, the second shape of the measurement target being a three-dimensional (3D) shape of the measurement target generated based on the determined positional relationship between the positions of the at least three markers and the first shape of the measurement target, the guide of the position to be acquired next being a line to be traced next to be followed along the measurement target using the stylus pen, the line to be traced next not connected to and not comprising the fiducial points of the measurement target and tracing the first shape of the measurement target; and receive a second signal transmitted from the stylus pen as the stylus pen is moved along the line to be traced next, the second signal continuously providing position information of the stylus pen, wherein the stylus-pen is configured to be in direct contact with the measurement target as the second signal is transmitted.

15. The measurement system according to claim 14, further comprising:

a magnetic resonance imaging (MRI) device configured to obtain a 3D MRI image of the measurement target; and the input device is further configured to use the obtained 3D MRI image as the second shape of the measurement target.

16. The measurement system according to claim 14, wherein the input device is further configured to display the generated screen by displaying at least one line corresponding to the second signal on the second shape of the measurement target.

17. The measurement system according to claim 15, wherein the input device is further configured to:
   alter the 3D MRI image of the measurement target based on the position information received from the stylus pen.

18. The measurement system according to claim 15, wherein the input device is further configured to:
   translate a coordinate system corresponding to the MRI device to a coordinate system corresponding to the cerebral-function measuring device, wherein the cerebral-function measuring device is at least one of a magnetoencephalography device configured to measure magneto-encephalography (MEG), and an electroencephalograph device configured to measure electroencephalography (EEG).

19. A non-transitory computer-readable medium including programmed instructions for a computer, which when executed by the computer, cause the computer to:
   receive a first signal transmitted from a stylus pen, the first signal including position information of at least three markers adapted to be attached to a measurement target and detectable by a cerebral-function measuring device, the position information corresponding to a first shape of the measurement target, the at least three markers corresponding to fiducial points of the measurement target;
   determine positional relationship between a position of the at least three markers and the first shape of the measurement target based on the position information;
   generate a screen in which a second shape of the measurement target and a guide of a position to be acquired next with the stylus pen are superimposed, the second shape of the measurement target being a three-dimensional (3D) shape of the measurement target generated based on the determined positional relationship between the positions of the at least three markers and the first shape of the measurement target, the guide of the position to be acquired next being a line to be traced next to be followed along the measurement target using the stylus pen, the line to be traced next not connected to and not comprising the fiducial points of the measurement target;
   receive a second signal transmitted from the stylus pen as the stylus pen is moved along the line to be traced next, the second signal continuously providing position information of the stylus pen, wherein the stylus pen is configured to be in direct contact with the measurement target as the second signal is transmitted; and
   display the generated screen on a display unit.

* * * * *